US 8,457,372 B2

(12) United States Patent
Fu et al.

(10) Patent No.: US 8,457,372 B2
(45) Date of Patent: Jun. 4, 2013

(54) SUBTRACTION OF A SEGMENTED ANATOMICAL FEATURE FROM AN ACQUIRED IMAGE

(75) Inventors: Dongshan Fu, Santa Clara, CA (US); Gopinath Kuduvalli, San Jose, CA (US); Hui Zhang, Sunnyvale, CA (US)

(73) Assignee: Accuray Incorporated, Sunnyvale, CA (US)

( * ) Notice: Subject to any disclaimer, the term of this patent is extended or adjusted under 35 U.S.C. 154(b) by 775 days.

(21) Appl. No.: 12/242,609

(22) Filed: Sep. 30, 2008

(65) Prior Publication Data
US 2010/0080354 A1 Apr. 1, 2010

(51) Int. Cl.
*G06K 9/00* (2006.01)

(52) U.S. Cl.
USPC .......................................... 382/128

(58) Field of Classification Search
None
See application file for complete search history.

(56) References Cited

U.S. PATENT DOCUMENTS

| | | | |
|---|---|---|---|
| 5,901,199 A | 5/1999 | Murphy et al. | |
| 6,307,914 B1 | 10/2001 | Kunieda et al. | |
| 6,501,981 B1 | 12/2002 | Schweikard et al. | |
| 7,204,640 B2 | 4/2007 | Fu et al. | |
| 7,327,865 B2 | 2/2008 | Fu et al. | |
| 7,720,196 B2 * | 5/2010 | Zhang et al. | 378/65 |
| 7,756,567 B2 * | 7/2010 | Kuduvalli et al. | 600/427 |
| 2004/0042583 A1 | 3/2004 | Wackerle et al. | |
| 2004/0092815 A1 | 5/2004 | Schweikard et al. | |
| 2005/0075563 A1 | 4/2005 | Sukovic et al. | |
| 2006/0274885 A1 | 12/2006 | Wang et al. | |
| 2008/0037843 A1 | 2/2008 | Fu et al. | |
| 2008/0130825 A1 | 6/2008 | Fu et al. | |
| 2011/0019896 A1 * | 1/2011 | Fu et al. | 382/132 |
| 2011/0116703 A1 * | 5/2011 | Fu et al. | 382/132 |

OTHER PUBLICATIONS

Coste-Maniere, E., et al., "Robotic Whole Body Stereotactic Radiosurgery: Clinical Advantages of the CyberKnife® Integrated System," The International Journal of Medical Robotics and Computer Assisted Surgery, 2005, www.roboticpublications.com, pp. 28-39.
PCT International Search Report, International Application No. PCT/US07/21884, filed Oct. 11, 2007, mailed Apr. 2, 2008, 4 pages.
PCT Written Opinion of the International Searching Authority, International Application No. PCT/US07/21884, filed Oct. 11, 2007, mailed Apr. 2, 2008, 8 pages.
Woods, Roger P., "Spatial Transformation Models," Chapter 29, IV Registration, Handbook of Medical Imaging, Processing and Analysis, Editor-in-Chief, Isaac N. Bankman, 2000, Academic Press, pp. 465-490.
Grimson, Eric, et al., "Registration for Image-Guided Surgery," Chapter 30, IV Registration, Handbook of Medical Imaging, Processing and Analysis, Editor-in-Chief, Isaac N. Bankman, 2000, Academic Press, pp. 623-633.
Russakoff, Daniel B., et al., "Fast Generation of Digitally Reconstructed Radiographs using Attenuation Fields with Application to 2D-3D Image Registration," IEEE Transactions on Medical Imaging, vol. 24, No. 11, Nov. 2005, pp. 1441-1454.

(Continued)

*Primary Examiner* — Jermele M Hollington
(74) *Attorney, Agent, or Firm* — Lowenstein Sandler LLP

(57) ABSTRACT

A system, method and apparatus for subtracting a synthetically-generated image, including a segmented anatomical feature, from an acquired image.

44 Claims, 8 Drawing Sheets

OTHER PUBLICATIONS

Rogowska, Jadwiga, "Overview and Fundamentals of Medical Image Segmentation," Chapter 5, II Segmentation, Handbook of Medical Imaging, Processing and Analysis, Editor-in-Chief, Isaac N. Bankman, 2000, Academic Press, pp. 69-85.

Dawant, Benoit M., et al., "Image Segmentation," Chapter 2, Handbook of Medical Imaging, vol. 2, Medical Image Processing and Analysis, Editors Milan Sonka and J. Michael Fitzpatrick, 2000, The Society of Photo-Optical Instrumentation Engineers, pp. 71-127.

Gonzalez, Rafael C., et al., "Digital Image Processing," Addison-Wesley Publishing Company, Jun. 1992, pp. 170-185.

PCT International Search Report, PCT/US2009/056526 filed Sep. 10, 2009, mailed Nov. 5, 2009, 13 pages.

International Preliminary Report on Patentability mailed Apr. 14, 2011, for PCT Patent Application No. PCT/US2009/056526, filed Sep. 10, 2009, 7 pages.

* cited by examiner

US 8,457,372 B2

SUBTRACTION OF A SEGMENTED ANATOMICAL FEATURE FROM AN ACQUIRED IMAGE

TECHNICAL FIELD

Embodiments of the invention are related to image-guided radiation treatment systems and, in particular, to subtracting segmented anatomical features of a synthetically-generated image from an acquired image to improve the visibility of tumors in the acquired image in image-guided radiation treatment systems.

BACKGROUND

Image-guided radiosurgery and radiotherapy systems (image-guided radiation treatment systems, collectively) are radiation treatment systems that use external radiation beams to treat pathological anatomies (e.g., tumors, lesions, vascular malformations, nerve disorders, etc.) by delivering a prescribed dose of radiation (e.g., x-rays or gamma rays) to the pathological anatomy while minimizing radiation exposure to surrounding tissue and critical anatomical structures (e.g., the spinal cord). Both radiosurgery and radiotherapy are designed to necrotize or damage the pathological anatomy while sparing healthy tissue and the critical structures. Radiotherapy is characterized by a low radiation dose per treatment (1-2 Gray per treatment), and many treatments (e.g., 30 to 45 treatments). Radiosurgery is characterized by a relatively high radiation dose (typically 5 Gray or more per treatment) in one to five treatments (1 Gray equals one joule per kilogram). Image-guided radiosurgery and radiotherapy systems eliminate the need for invasive frame fixation by tracking patient pose (position and orientation) during treatment. In addition, while frame-based systems are generally limited to intracranial therapy, image-guided systems are not so limited.

Image-guided radiotherapy and radiosurgery systems include gantry-based systems and robotic-based systems. In gantry-based systems, a radiation source is attached to a gantry that moves around a center of rotation (isocenter) in a single plane. Each time a radiation beam is delivered during treatment, the axis of the beam passes through the isocenter. Treatment angles are therefore limited by the rotation range of the radiation source and the degrees of freedom of a patient positioning system. In robotic-based systems, the radiation source is not constrained to a single plane of rotation, having five or more degrees of freedom.

In conventional image-guided radiation treatment systems, patient tracking during treatment is accomplished by comparing two-dimensional (2D) in-treatment x-ray images of the patient to 2D digitally reconstructed radiographs (DRRs) derived from the three dimensional (3D) pre-treatment imaging data that is used for diagnosis and treatment planning. The pre-treatment imaging data may be computed tomography (CT) data, magnetic resonance imaging (MRI) data, positron emission tomography (PET) data or 3D rotational angiography (3DRA), for example. Typically, the in-treatment x-ray imaging system is stereoscopic, producing images of the patient from two or more different points of view (e.g., orthogonal), and a corresponding DRR is generated for each point of view. A DRR is a synthetic x-ray image generated by casting (mathematically projecting) rays through a 3D image, simulating the geometry of the in-treatment x-ray imaging system. The resulting DRR then has the same scale and point of view as the in-treatment x-ray imaging system. To generate a DRR, the 3D imaging data is divided into voxels (volume elements) and each voxel is assigned an attenuation (loss) value derived from the 3D imaging data. The relative intensity of each pixel in a DRR is then the summation of the voxel losses for each ray projected through the 3D image. Different patient poses are simulated by performing 3D transformations (rotations and translations) on the 3D imaging data before the DRR is generated. The 3D transformation and DRR generation may be performed iteratively in real time, during treatment, or alternatively, the DRRs (in each projection) corresponding to an expected range of patient poses may be pre-computed before treatment begins.

Each comparison of an in-treatment x-ray image with a DRR produces a similarity measure or, equivalently, a difference measure (e.g., cross correlation, entropy, mutual information, gradient correlation, pattern intensity, gradient difference, image intensity gradients) that can be used to search for a 3D transformation that produces a DRR with a higher similarity measure to the in-treatment x-ray image (or to search directly for a pre-computed DRR as described above). When the similarity measure is sufficiently maximized (or equivalently, a difference measure is minimized), the 3D transformation corresponding to the DRR can be used to align the 3D coordinate system of the treatment plan with the 3D coordinate system of the treatment delivery system, to conform the relative positions of the radiation source and the patient to the treatment plan. In the case of pre-computed DRRs, the maximum similarity measure may be used to compute a differential 3D transformation between the two closest DRRs. FIG. 1 illustrates the process described above for the case of in-treatment DRR generation.

One limiting factor in the accuracy of the registration and tracking algorithms is that bony structures, such as a spinal structure, may partially or completely block the tumor in one or more of the projections, reducing the visibility of the tumor in the corresponding projection in the in-treatment x-ray images.

BRIEF DESCRIPTION OF THE DRAWINGS

The present invention is illustrated by way of example, and not by limitation, in the figures of the accompanying drawings in which.

DETAILED DESCRIPTION

Figure 1:
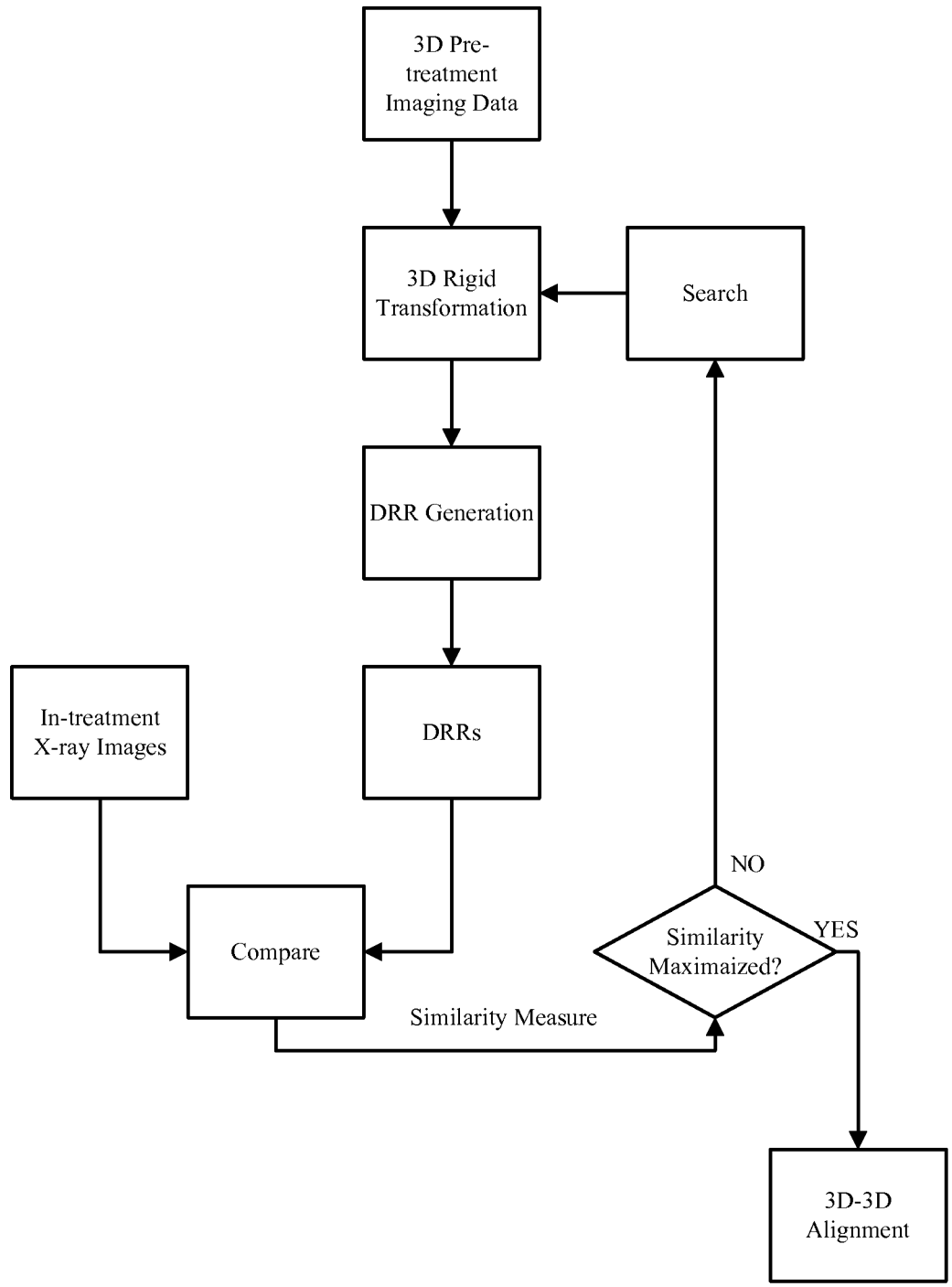
FIG. 1 illustrates 2D-3D registration in a conventional image-guided radiation treatment system.

Described herein is a method for subtracting a synthetically-generated image, including a segmented anatomical feature, from an acquired image. In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. The term "x-ray image" as used herein may mean a visible x-ray image (e.g., displayed on a video screen) or a digital representation of an x-ray image (e.g., a file corresponding to the pixel output of an x-ray detector). The terms "in-treatment image," "live image," or "acquired image," as used herein, may refer to images acquired at any point in time during a treatment delivery phase of a radiosurgery or radiotherapy procedure, which may include times when the radiation source is either on or off. The term "DRR," as described above, may refer to a synthetically-generated image. From time to time, for convenience of description, CT imaging data may be used herein as an exemplary 3D imaging modality. It will be appreciated that data from any type of 3D imaging modality, such as CT data, MRI data, PET data, 3DRA data, or the like, may also be used in various embodiments of the invention.

The embodiments described herein may be used in the context of tracking a tumor during treatment. Initially, vertebral structures of a patient's anatomy, such as the vertebral structures of the spine, may be registered with the pre-treatment CT scans. This registration is used to correct for patient alignment with the pre-treatment CT scans, before the tumor (e.g., lung tumor) itself is tracked directly. As described above, difficulties arise when the spinal structure completely blocks the lung tumor in one of the projections, reducing the visibility of the lung tumor in the corresponding projection in the live images. This visibility can be improved using the embodiments described herein, leading to improved tracking performance.

In one embodiment of subtracting a spinal structure, the system performs image segmentation on a 3D medical image (such as CT, MRI, PET, 3DRA image, or the like). Medical image segmentation is the process of partitioning the 3D medical image into regions that are homogeneous with respect to one or more characteristics or features (e.g., tissue type, density). Image segmentation may be used to differentiate the targeted pathological anatomy and critical anatomy structures to be avoided (e.g., spinal cord). The results of the image segmentation are used in treatment planning to plan the delivery of radiation to the pathological anatomy. The results of the image segmentation may be used to generate DRRs of the pathological anatomy and one or more anatomical features. In radiation treatment systems (including both frame-based and image-guided), segmentation may be a step performed in treatment planning where the boundaries and volumes of a targeted pathological anatomy (e.g., a tumor or lesion) and other anatomical features, such as critical anatomical structures (e.g., bony or muscular structures), are defined and mapped into the treatment plan. The precision of the segmentation may be used in obtaining a high degree of conformality and homogeneity in the radiation dose during treatment of the pathological anatomy, while sparing healthy tissue from unnecessary radiation.

For example, in on embodiment, as part of segmentation, a spine volume of interest (VOI) in the 3D CT volume is segmented. From the spine VOI, a spine DRR can be generated. The spine DRR is a synthetically-generated image that includes the segmented spine.

The system then acquires and processes an x-ray image, and performs spine registration between the acquired x-ray image and the spine DRR to align the spine. After registering the spine structure in the live images with that in the DRR, the exact transformation required to transform the spine structure in the DRR images to those in the live images may be determined.

After the spine has been aligned, the system acquires and processes an x-ray image for lung tracking. The system adjusts the DRR image contracts to match the acquired x-ray image contrast, and subtracts the spine DRR from the acquired x-ray image to enhance the visibility of the lung tumor in the acquired x-ray image. The system then performs registration of the x-ray image with the spine removed and a tumor DRR, which is generated from the 3D CT volume like the spine DRR described above.

Although the above embodiment describes subtracting the spine for tracking a lung tumor, in other embodiments, VOIs having other types of pathological anatomies than a lung tumor, and other anatomical features than a spinal structure, may be used, such as bony structures, muscular structures, or the like. For example, the bony structures may include portions of a spine, a cranium, a sacrum, a rib, or the like, and the muscular structures may include portions of a heart, a prostate, an organ, or the like.

Figure 2:
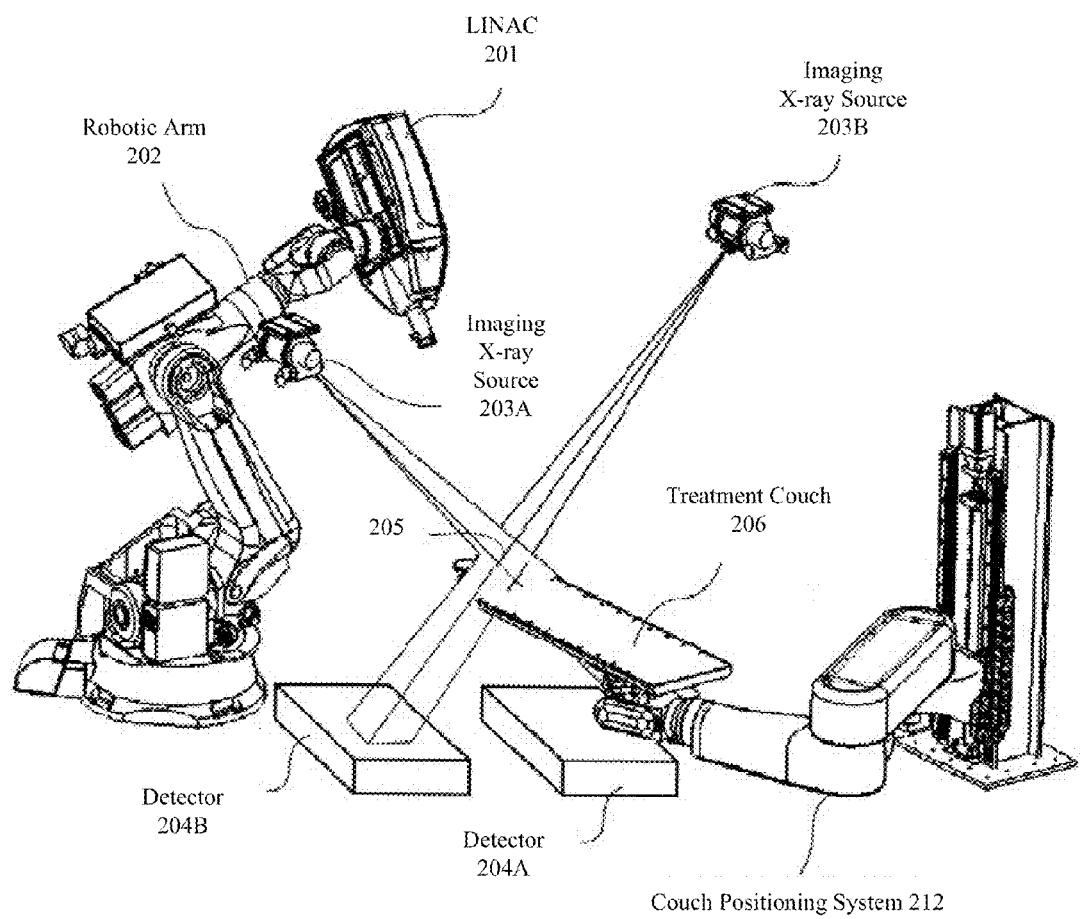
FIG. 2 illustrates an image-guided robotic radiosurgery system in one embodiment.

FIG. 2 illustrates the configuration of an image-guided, robotic-based radiation treatment system 200, which may be used to implement embodiments of the present invention. In FIG. 2, the radiation treatment source is a linear accelerator (LINAC) 201 mounted on the end of a robotic arm 202 having multiple (e.g., 5 or more) degrees of freedom in order to position the LINAC 201 to irradiate a pathological anatomy (target region or volume) with beams delivered from many angles, in many planes, in an operating volume around the patient. Treatment may involve beam paths with a single isocenter, multiple isocenters, or with a non-isocentric approach.

The treatment delivery system of FIG. 2 includes an in-treatment imaging system, which may include x-ray sources 203A and 203B and x-ray detectors (imagers) 204A and 204B. The two x-ray sources 203A and 203B may be mounted in fixed positions on the ceiling of an operating room and may be aligned to project imaging x-ray beams from two different angular positions (e.g., separated by 90 degrees) to intersect at a machine isocenter 205 (which provides a reference point for positioning the patient on a treatment couch 206 during treatment using a couch positioning system 212) and to illuminate imaging planes of respective detectors 204A and 204B after passing through the patient. In other embodiments, system 200 may include more or less than two x-ray sources and more or less than two detectors, and any of the detectors may be movable rather than fixed. In yet other embodiments, the positions of the x-ray sources and the detectors may be interchanged.

The detectors 204A and 204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with the reference images during the registration process.

In one embodiment, the image-guided, robotic-based radiation treatment system 200 is the CYBERKNIFE® system, developed by Accuray Incorporated of Sunnyvale, Calif. Alternatively, other systems may be used. Also, although the treatment couch 206 is coupled to a robotic arm of the couch positioning system 212 in FIG. 2, in other embodiments, other patient positioning systems may be used to position and orient the patient relative to the LINAC 201. For example, the LINAC 201 may be positioned with respect to a treatment couch 206 that is not coupled to a robotic arm, such as a treatment couch mounted to a stand, to the floor, to the AXUM® treatment couch, developed by Accuray Inc., of Sunnyvale, Calif., or to other patient positioning systems.

The operations of this and other flow diagrams will be described with reference to the exemplary embodiments of the other diagrams. However, it should be understood that the operations of the flow diagrams can be performed by embodiments of the invention other than those discussed with reference to these other diagrams, and the embodiments of the invention discussed with reference these other diagrams can perform operations different than those discussed with reference to the flow diagrams.

The techniques shown in the figures can be implemented using code and data stored and executed on one or more computers. Such computers store code and data using machine-readable storage media (e.g., magnetic disks; optical disks; random access memory; read only memory; non-volatile memory devices). In addition, such computers typically include a set of one or more processors coupled to one or more other components, such as a storage device, a number of user input/output devices (e.g., a keyboard and a display), and a network connection. The coupling of the set of processors and other components is typically through one or more busses and bridges (also termed as bus controllers). The storage device represents one or more machine storage media. Thus, the storage device of a given computer system typically stores code and data for execution on the set of one or more processors of that computer. Of course, one or more parts of an embodiment of the invention may be implemented using different combinations of software, firmware, and hardware.

Figure 3:
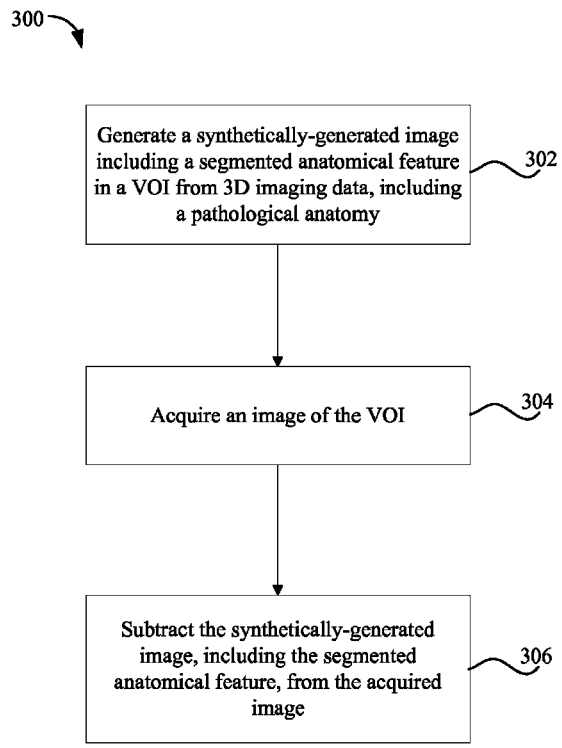
FIG. 3 is a flow diagram of one embodiment of a method 300 for subtracting segmented anatomical features of a synthetically-generated image from an acquired image according to one embodiment.

FIG. 3 is a flow diagram of one embodiment of a method 300 for subtracting segmented anatomical features of a synthetically-generated image from an acquired image according to one embodiment. The method 300 is performed by processing logic that may include hardware (circuitry, dedicated logic, or the like), software (such as is run on a general-purpose computer system or a dedicated machine), or a combination of both. In one embodiment, method 300 is performed by a processing device of the treatment delivery system. In another embodiment, the method 300 is performed by a processing device of the treatment planning system. Alternatively, the method 300 may be performed by a combination of the treatment planning system and the treatment delivery system.

Processing logic generates a synthetically-generated image (e.g., DRR), including a segmented anatomical feature in a VOI, from the 3D imaging data (block 302). The VOI also includes a pathological anatomy (e.g., tumor or other target). The processing logic acquires an image of the VOI (block 304). The processing logic subtracts the synthetically-generated image (e.g., DRR), including the segmented anatomical feature, from the acquired image (block 306).

Figure 4:
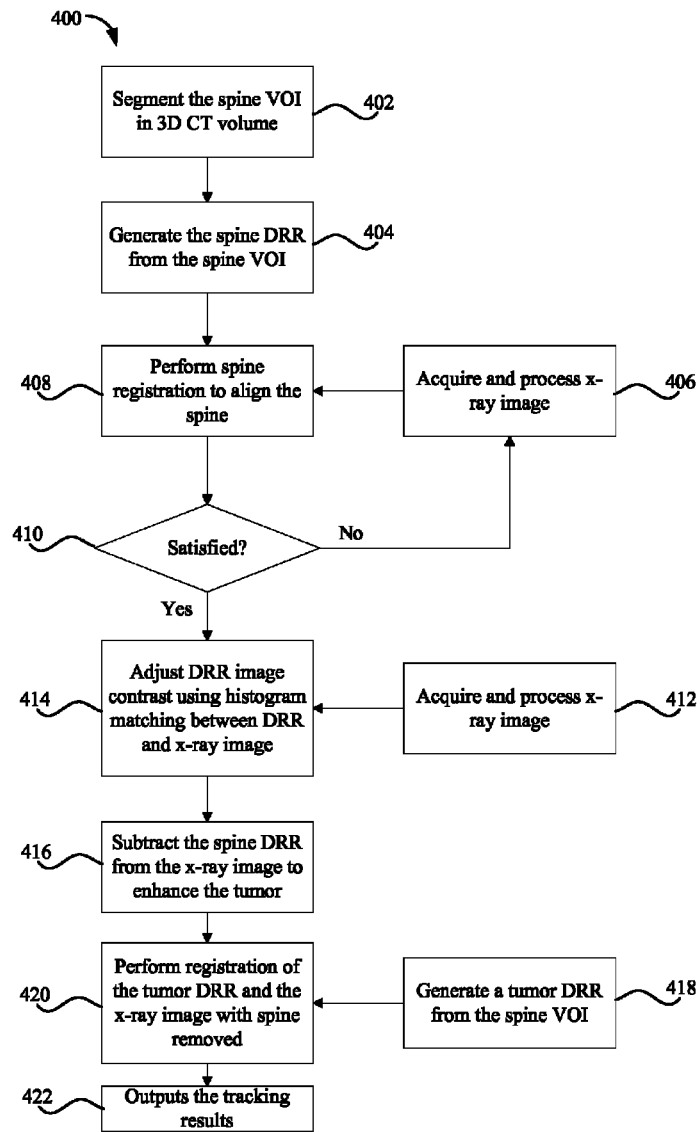
FIG. 4 is a flow diagram of another embodiment of a method 400 for subtracting a segmented spinal structure of a synthetically-generated image from an acquired image according to one embodiment.

FIG. 4 is a flow diagram of another embodiment of a method 400 for subtracting a segmented spinal structure of a synthetically-generated image from an acquired image according to one embodiment. The method 400 is performed by processing logic that may include hardware (circuitry, dedicated logic, or the like), software (such as is run on a general-purpose computer system or a dedicated machine), or a combination of both. In one embodiment, method 400 is performed by a processing device of the treatment delivery system. In another embodiment, the method 400 is performed by a processing device of the treatment planning system. Alternatively, the method 400 may be performed by a combination of the treatment planning system and the treatment delivery system.

The processing logic segments a VOI containing a portion of a patient's spine (block 402) from the 3D imaging data. The VOI includes the spinal structure or other anatomical anatomy. The purpose of using an anatomical VOI is to remove anatomical structures in a 3D image volume so that a tumor in 2D projections has a better visibility. Therefore, the tumor (e.g., lung tumor) may not be included in the anatomical VOI. The VOI may include a set of 2D contours in one or more views of the 3D imaging data. The processing logic segments the VOI to obtain the segmented spine and the segmented tumor. The processing logic may segment the VOI by generating a 3D voxel mask, which is configured to delineate the spine (e.g., anatomical feature to be subtracted) and to exclude other anatomical features external to the spine. The 3D voxel mask may be generated from a set of 2D contours. In another embodiment, the 3D voxel masks may be multiple multi-bit voxel masks, where each bit in a multi-bit voxel mask corresponds to a different VOI. The processing logic generates the spine DRR from the spine VOI (block 404). The processing logic generates the DRR from 3D transformations of the segmented spine in each of two or more projections. The processing logic acquires and process an x-ray image (block 406), and performs spine registration to align the spine (block 408). In particular, the processing logic registers the acquired x-ray image with the spine DRR to know the exact transformation required to transform the spine structure in the DRR image to those in the acquired live images. After alignment, if a translation is performed to bring the tumor (e.g. lung tumor) into the imaging field of view, the transformation can take the amount of couch motion into account. As part of the spine segmentation, the processing logic may convert the image geometry of the synthetically-generated image to the image geometry of the acquired image. The processing logic determines if the spine registration has been satisfied (block 410). If not, the processing logic returns to block 406 to acquire and process another x-ray image to perform additional spine registration at block 408 until the spine registration is satisfied at block 410.

Once the spine registration is satisfied, the processing logic acquires and processes an x-ray image (block 412), and adjusts an image contrast of the spine DRR image with an image contrast of the acquired image at block 412 (block 414). To subtract the bony structure (spine) from the live x-ray image, the intensity of the DRR image should be well matched with the acquired x-ray images. In one embodiment, matching the image contrast of the spine DRR and the image contrast of the acquired image may be done performed using a local histogram equalization algorithm. The processing logic adjusts the local dynamic range of two images. The dynamic range may be defined as the minimum and maximum of effective intensity in the range. The intensity of his dynamic range is then normalized to the range [0.0, 1.0] in both the DRR and the acquired image. The dynamic range adjustment is local, because it only normalizes part of all intensities, for example, approximately 30% to 90%. After, the histogram equalization algorithm may be used to stretch target and reference images to find the final adjustment. In one embodiment, the final intensity match functions are computed as represented in the three following formulas:

$$\overline{I}_{Xray} = LUT_{Xray}(I_{Xray}) \quad (1)$$

$$\overline{I}_{DRR} = LUT_{DRR}(I_{DRR}) \quad (2)$$

$$I_{MatchDRR} = LUT_{Xray}^{-1}(LUT_{DRR}(I_{DRR})) \quad (3)$$

The variable $I_{Xray}$ is the intensity from the normalized image from dynamic range adjustment, and $\bar{I}_{Xray}$ is the intensity from histogram equalization, as shown in the formula (1). The variable $I_{DRR}$ is the intensity from the normalized image from dynamic range adjustment, and $\bar{I}_{DRR}$ is the intensity from histogram equalization, as shown in the formula (2). The final pixel intensity, $I_{MatchDRR}$, of the matched DRR is computed using the formula (3). The matched DRR will have a similar histogram and similar image intensity as the X-ray image, which allows the subtraction of spine DRR from the X-ray image to enhance the tumor visibility. In one embodiment, after the histogram equalization of the DRR with respect to the X-ray image, the DRR image intensity (the first image) is automatically adjusted to match the X-ray image (the second image). The purpose of histogram equalization between the spine DRR and the X-ray image is to make the image intensity of the spine DRR similar to that of the X-ray image.

The processing logic subtracts the adjusted spine DRR from the acquired x-ray image to enhance the tumor (or other anatomical features) (block 416). The processing logic generates a tumor DRR from the spine VOI (block 418). In one embodiment, the processing logic generates the tumor DRR when it generates the spine DRR at block 404. The processing logic performs registration of the tumor DRR and the acquired x-ray image with the spine removed at block 416 (block 420), and outputs the tracking results (block 422).

It should be noted that acquired x-ray images may be 2D projections of the spine VOI in real-time. The spine VOI may include a set of 2D contours in one or more views of the 3D imaging data. The 3D imaging data may be received from a medical imaging system. Alternatively, the 3D imaging data may be acquired from imaging devices that are part of the treatment planning or treatment delivery systems. The 3D imaging data may include CT image data, MR image data, PET image data, 3DRA image data for treatment planning, or the like.

In one embodiment, the processing logic performs the registration at block 408 by comparing the spine DRR in each projection with the corresponding acquired image (at block 406) to produce a similarity measure in each projection. The acquired image at block 406 may be a 2D in-treatment image. Each comparison of an in-treatment x-ray image with a DRR produces a similarity measure or, equivalently, a difference measure (e.g., cross correlation, entropy, mutual information, gradient correlation, pattern intensity, gradient difference, image intensity gradients) that can be used to search for a 3D transformation that produces a DRR with a higher similarity measure to the in-treatment x-ray image (or to search directly for a pre-computed DRR as described above). The processing logic computes a 3D rigid transformation corresponding to a maximum similarity measure in each projection. The maximum similarity measure corresponds to registration between the spine DRR in each projection and the corresponding 2D in-treatment image. The processing logic computes the 3D rigid transformation from a transformation between the spine DRR in each projection and the corresponding 2D in-treatment image. In one embodiment, the similarity measure in each projection includes a vector displacement field between the corresponding DRR and the corresponding 2D in-treatment image. The processing logic may also determine an average rigid transformation of the segment VOI from the vector displacement field in each projection. In one embodiment, the processing logic computes the 3D rigid transformations corresponding to the maximum similarity measure in each projection by computing a similarity measure between a DRR in each projection and the corresponding 2D in-treatment image, and selecting a transformation of the 3D segmented region from the similarity measure that generates another DRR in each projection having an increased similarity measure with the corresponding 2D in-treatment image.

When the similarity measure is sufficiently maximized (or equivalently, a difference measure is minimized), the 3D transformation corresponding to the DRR can be used to align the 3D coordinate system of the treatment plan with the 3D coordinate system of the treatment delivery system, to conform the relative positions of the radiation source and the patient to the treatment plan. In the case of pre-computed DRRs, the maximum similarity measure may be used to compute a differential 3D transformation between the two closest DRRs.

In one embodiment, the processing logic performs the registration at block 420 in a similar manner as described above with respect to block 408, except the registration is between the tumor DRR and the acquired image at block 418.

In one embodiment, the processing logic determines 3D coordinates of the tumor (e.g., pathological anatomy), and positions a radiation treatment beam source, such as the LINAC 201, using the 3D coordinates of the tumor such that a radiation beam emitted from the radiation treatment beam source is directed to the tumor. In another embodiment, the processing logic determines 3D coordinates of the tumor (e.g., pathological anatomy), and positions a patient using 3D coordinates of the tumor such that a radiation beam emitted from a radiation treatment beam source is directed to the tumor. Alternatively, the processing logic may position both the radiation treatment beam source and the patient.

Although the above embodiment describes subtracting the spine for tracking a lung tumor, in other embodiments, VOIs having other types of pathological anatomies than a lung tumor, and other anatomical features than a spinal structure, may be used, such as bony structures, muscular structures, or the like. For example, the bony structures may include portions of a spine, a cranium, a sacrum, a rib, or the like, and the muscular structures may include portions of a heart, a prostate, an organ, or the like.

The VOI of the CT image volume may be defined by a stack of contours, each contour being defined on a corresponding plane parallel to a slice of the CT image volume. A contour is usually represented as a set of points, which may be interpolated to obtain closed contours. The CT volume may be divided into voxels having the same resolution as the original CT imaging data. The voxels in the CT image volume may be masked by a 3D binary mask (i.e., a mask for each voxel in the 3D CT image volume). The 3D binary mask may be defined as a single-bit binary mask set having a single-bit mask for each voxel in the CT image volume or as a multi-bit mask set having a multi-bit mask for each voxel in the CT image volume. A single-bit binary mask can select or deselect voxels in the CT image volume to define a single VOI. For example, the single bit value may be set to 1 for voxels that lie inside the VOI defined by the contours and 0 for voxels that lie outside of the VOI defined by the contours. A multi-bit mask allows multiple volumes of interest to be encoded in one 3D binary mask, with each bit corresponding to one VOI.

The process described above may be automated by a spine segmentation tool, such as the tool provided in the MULTI-PLAN® treatment planning system, developed by Accuray Incorporated of Sunnyvale, Calif. The segmentation tool may be used to manipulate a patient's medical image (e.g., CT or other image volumes such as MRI, PET, etc.). Alternatively, other treatment planning systems may be used.

Figure 5:
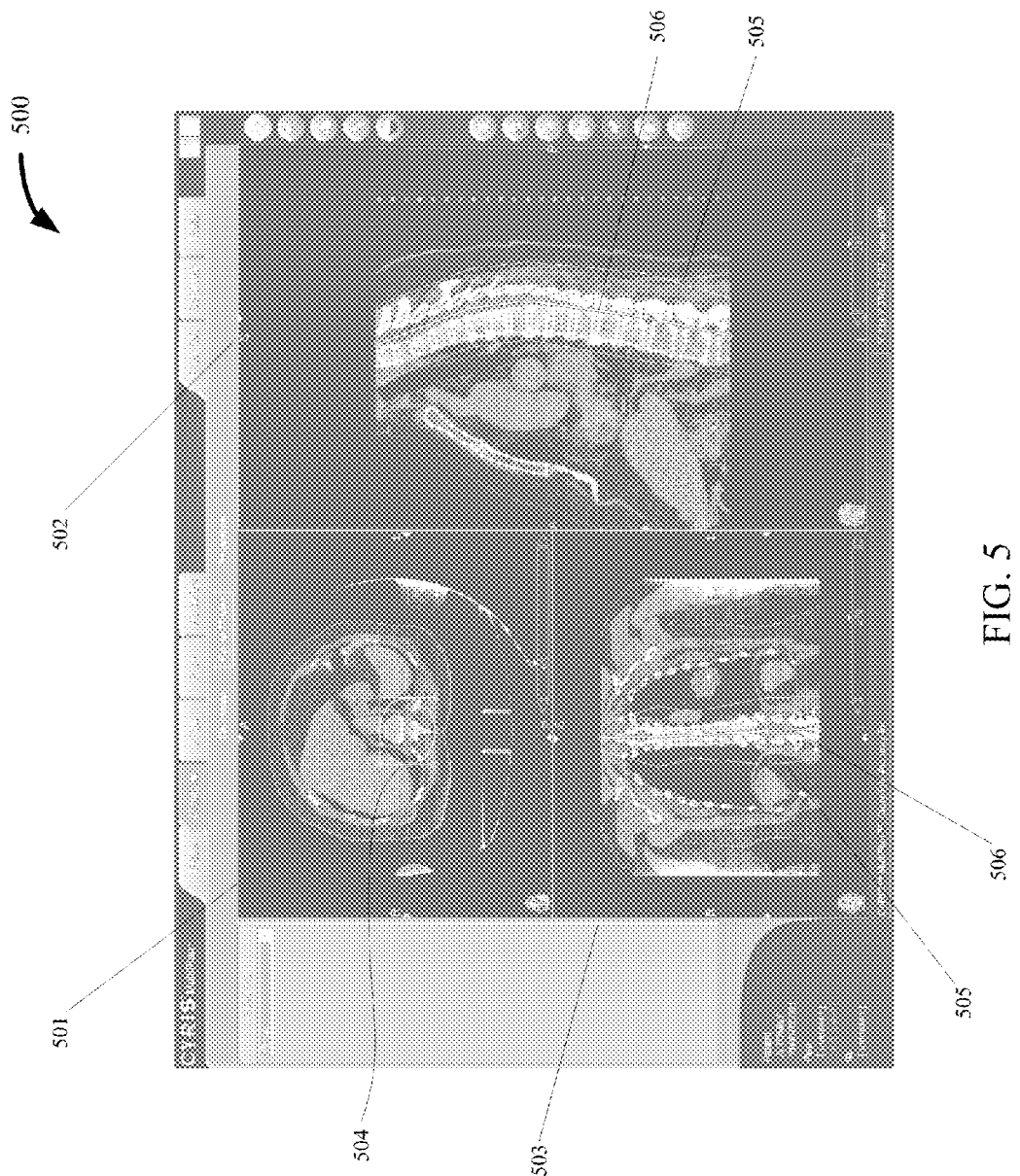
FIG. 5 is a screen shot illustrating how a segmentation tool allows a user to delineate a spine volume of interest simultaneously from three cutting planes of the medical image.

FIG. 5 is a screenshot 500 illustrating how the segmentation tool allows a user to delineate a spine volume of interest simultaneously from three cutting planes of the medical image: the axial plane 501, the sagittal plane 502, and the coronal plane 503. On the axial plane 501, a two-dimensional contour is displayed. The contour can be a solid contour when it is defined by a user, or it can be a dashed-line contour interpolated from adjacent contours by a computer. A user can modify the contour by resizing it, scaling it or moving it. A user can also modify the shape of the contour to match the actual spine on the image slice being displayed by tweaking a shape morphing parameter. The shape morphing parameter defines how close the contour is to an ellipse. When the shape morphing parameter is set to 0, for example, the contour may be a standard ellipse. When the shape morphing parameter is set to 1, the contour may assume the outline of a spinal bone using automatic edge recognition methods as described, for example, in U.S. Pat. No. 7,327,865. By adjusting the morphing parameter in the range of [0, 1], the shape of the contour may be smoothly morphed from an ellipse, to a spinal bone. A user can also adjust the shape of the contour, for example, using control points on a bounding box of the contour.

On the sagittal plane 502 and coronal plane 503, a projected silhouette contour 505 of the spine volume of interest is displayed. The centers of all user-defined contours (such as contour 504, for example) are connected as the central axis of the spine 506. A user can move, add or remove contours by moving or dragging the centers of the contours. When the center of a contour is moved on the sagittal or coronal planes, the actual contour defined on the axial image slice is moved accordingly. When the user selects any point in between two center points of adjacent axial contours, a new contour is added at that position, with the contour automatically set to the interpolation of the two adjacent axial contours. When a user drags and drops the center point of a contour outside the region of the two adjacent contours, or outside the image boundary, the contour is removed from the volume of interest. Once the spine volume of interest is delineated and stored in the geometrical format, it is converted to the volume format as a three-dimensional image volume containing only the voxels within the volume of interest.

Figure 6A:
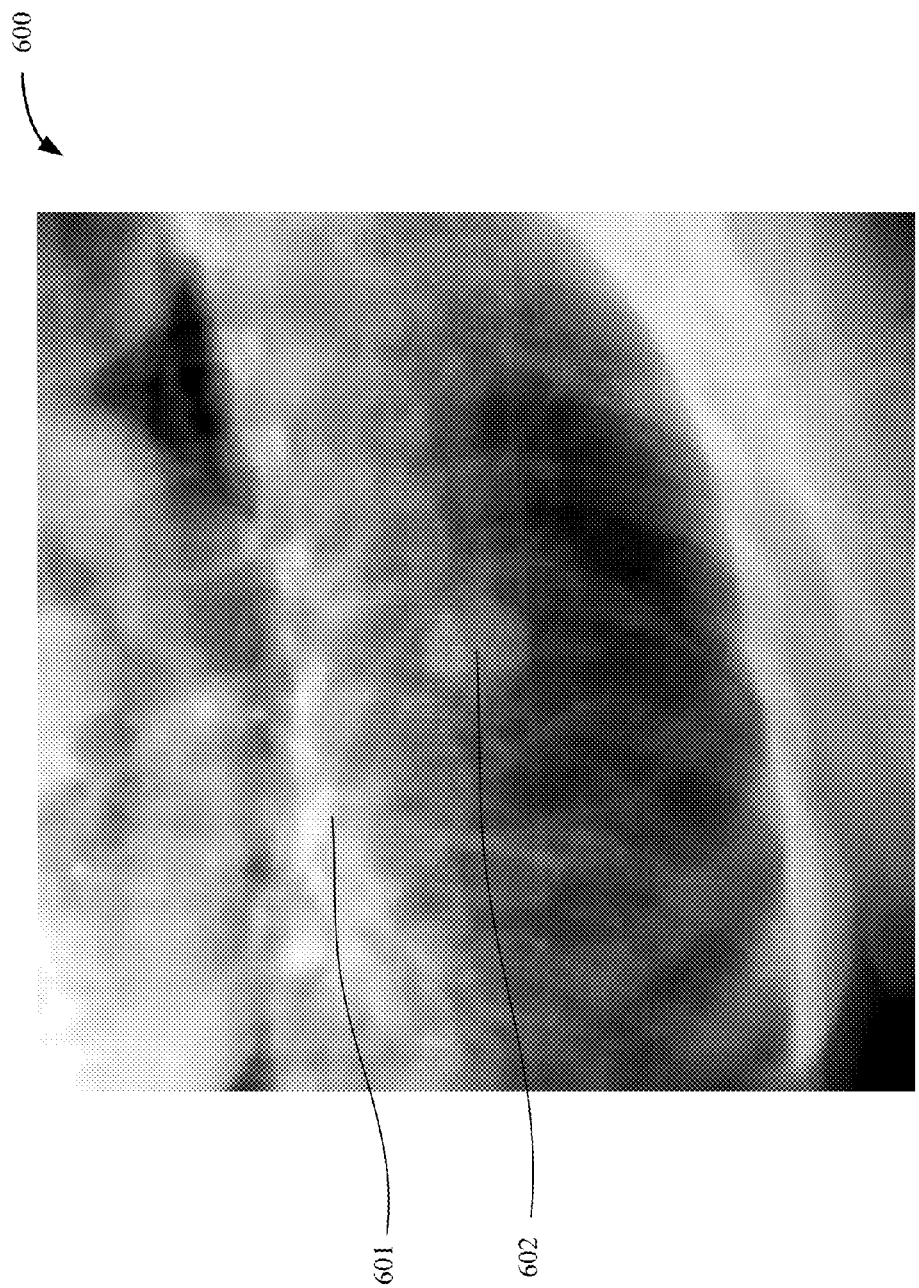
FIG. 6A is an acquired x-ray image of a volume of interest having a tumor according to one embodiment.

FIG. 6A is an acquired x-ray image of a volume of interest having a tumor according to one embodiment. The acquired x-ray image 600 has a spine 601 and a tumor 602. As described above, one limiting factor in the accuracy of the registration and tracking algorithms is that bony structures, such as the spine 602, may partially or completely block the tumor 601 in one or more of the projections, reducing the visibility of the tumor 602 in the corresponding projections in the in-treatment x-ray images. As described in the embodiments herein, the spine 602 can be subtracted from the x-ray image, as illustrated in FIG. 6B.

Figure 6B:
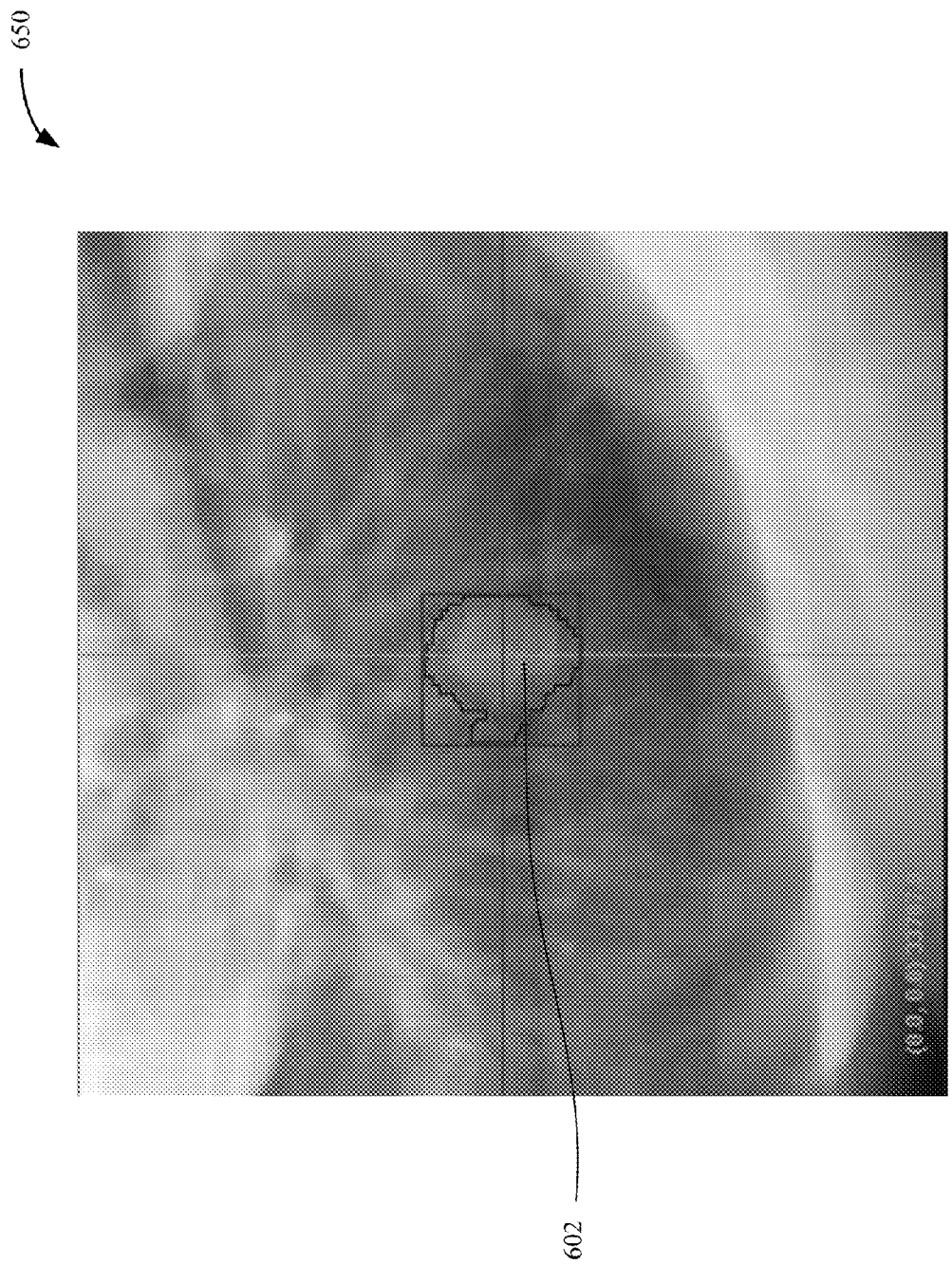
FIG. 6B is an x-ray image with the spine subtracted according to one embodiment.

FIG. 6B is an x-ray image with the spine subtracted according to one embodiment. As described above, the system may subtract the spine DRR (generated from the 3D CT volume), including the spine 601, from the acquired x-ray image 600 to enhance the visibility of the lung tumor 602 in the acquired x-ray image 650. The system may then performs registration of the x-ray image 650 with the spine 601 removed and a tumor DRR, which is generated from the 3D CT volume.

At the time of treatment, the 2D in-treatment x-ray images may be compared with the 2D DRRs and the results of the comparison to provide similarity measures. The similarity measures are used iteratively to find a 3D rigid transformation of the 3D imaging data that produces DRRs most similar to the in-treatment x-ray images. In the case of non-rigid structures (e.g., spine), more accurate registration may be manifested in improved accuracy of 2D displacement fields in each projection that describe the vector displacement at each point in the imaging field of view between the DRR and the in-treatment x-ray. The displacement fields in each projection may then be combined and averaged to determine an average rigid transformation, for example, as described in U.S. Pat. No. 7,327,865. Using the embodiments described herein, the segmented anatomical feature (e.g., spine) may be removed from the 2D in-treatment x-ray images before being registered with one or more DRRs, such as DRRs of the tumor. When the similarity measure is maximized, the corresponding 3D rigid transformation is selected to align the coordinate system of the 3D imaging data with the 3D coordinate system of the treatment delivery system (e.g., by moving the radiation source or the patient or by moving the radiation source and the patient). Also, the coordinates of a targeted pathological anatomy (as derived from treatment planning, for example) may be located, and radiation treatment may be applied to the pathological anatomy. In another embodiment, the results of 2D-2D image comparisons may be used to select from the pre-computed DRRs rather than to drive a 3D transformation function. Once the maximum similarity measure is found (based on the best-matching pre-computed DRRs), a 3D transformation may be extrapolated or interpolated from the DRRs for the 3D-3D alignment process. Here again, however, the DRRs are generated from 3D rigid transformations of the pre-segmentation 3D imaging data.

It will be apparent to one skilled in the art that the relationships between 3D pre-treatment imaging, 3D rigid transformations, DRRs, and in-treatment x-ray images. For example, U.S. Patent Publication No. 2008/0037843 and U.S. Patent Publication No. 2008/0130825 describe the relationship between 3D pre-treatment imaging, 3D rigid transformations, DRRs, and in-treatment x-ray images. In particular, the U.S. Patent Publication No. 2008/0130825 describes geometric relationships among the 3D coordinate system of a treatment delivery system, the 2D coordinate system of an in-treatment imaging system, and the 3D coordinate system of a 3D image (such as a pre-treatment CT image, for example). The embodiments described herein may be implemented in an image-guided radiation treatment system. Alternatively, embodiments of the present invention may also be implemented in other types of radiation treatment systems, including gantry-type image-guided radiation treatment systems, radiation treatment systems that generate DRR images in real-time or near real-time during treatment, or the like.

The methods and algorithms used to compare DRRs with in-treatment x-ray images and to compute similarity measures can be very robust and are capable of tracking both rigid and non-rigid (deformable) anatomical structures, such as the spine, without implanted fiducial markers. For non-rigid and deformable anatomical structures, such as the spine, registration and tracking are complicated by irreducible differences between DRRs derived from pre-treatment imaging and the x-ray images obtained during treatment (e.g., reflecting spinal torsion or flexing relative to the patient's pose during pre-treatment imaging). Methods for computing average rigid transformation parameters from such images have been developed to address the registration and tracking of non-rigid bodies. Such methods, including the calculation of vector displacement fields between DRRs and in-treatment x-ray images and 2D-2D registration and 2D-3D registration and tracking methods, are described in detail in U.S. Pat. No. 7,327,865. However, to the extent that DRRs are generated from unsegmented 3D imaging data and contain false details or lack true details, any similarity measure computed between a DRR image and an in-treatment x-ray image will have a lowered sensitivity to image differences.

Figure 7:
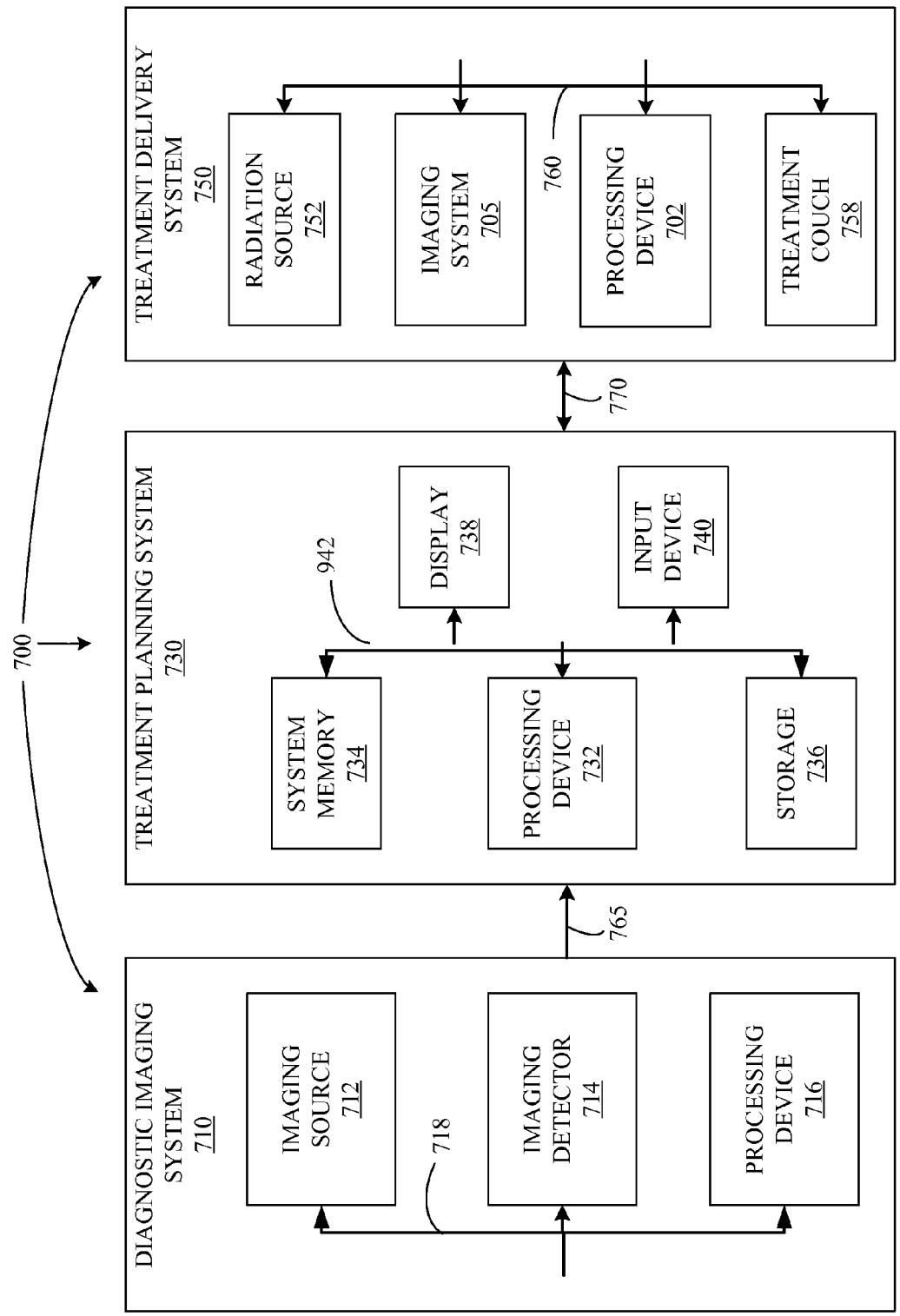
FIG. 7 illustrates a block diagram of one embodiment of a treatment system that may be used to perform radiation treatment in which embodiments of the present invention may be implemented.

FIG. 7 illustrates a block diagram of one embodiment of a treatment system 700 that may be used to perform radiation treatment in which embodiments of the present invention may be implemented. The depicted treatment system 700 includes a diagnostic imaging system 710, a treatment planning system 730, and a treatment delivery system 750. In other embodiments, the treatment system 700 may include fewer or more component systems.

The diagnostic imaging system 710 is representative of any system capable of producing medical diagnostic images of a VOI in a patient, which images may be used for subsequent medical diagnosis, treatment planning, or treatment delivery. For example, the diagnostic imaging system 910 is a computed tomography (CT) system, a single photon emission computed tomography (SPECT) system, a magnetic resonance imaging (MRI) system, a positron emission tomography (PET) system, a near infrared fluorescence imaging system, an ultrasound system, or another similar imaging system. For ease of discussion, any specific references herein to a particular imaging system, such as a CT x-ray imaging system (or another particular system), is representative of the diagnostic imaging system 710, generally, and does not preclude other imaging modalities, unless noted otherwise.

The illustrated diagnostic imaging system 710 includes an imaging source 712, an imaging detector 714, and a processing device 716. The imaging source 712, imaging detector 714, and processing device 716 are coupled to one another via a communication channel 718 such as a bus. In one embodiment, the imaging source 712 generates an imaging beam (e.g., x-rays, ultrasonic waves, radio frequency waves, etc.) and the imaging detector 714 detects and receives the imaging beam. Alternatively, the imaging detector 714 may detect and receive a secondary imaging beam or an emission stimulated by the imaging beam from the imaging source (e.g., in an MRI or PET scan). In one embodiment, the diagnostic imaging system 710 includes two or more diagnostic imaging sources 712 and two or more corresponding imaging detectors 714. For example, two x-ray sources 712 may be disposed around a patient to be imaged, fixed at an angular separation from each other (e.g., 90 degrees, 45 degrees, etc.) and aimed through the patient toward corresponding imaging detectors 714, which may be diametrically opposed to the imaging sources 714. A single large imaging detector 714 or multiple imaging detectors 714 may be illuminated by each x-ray imaging source 714. Alternatively, other numbers and configurations of imaging sources 712 and imaging detectors 714 may be used.

The imaging source 712 and the imaging detector 714 are coupled to the processing device 716 to control the imaging operations and process image data within the diagnostic imaging system 710. In one embodiment, the processing device 716 communicates with the imaging source 712 and the imaging detector 714. Embodiments of the processing device 716 may include one or more general-purpose processors (e.g., a microprocessor), special purpose processors such as a digital signal processor (DSP), or other types of devices, such as a controller or field programmable gate array (FPGA). The processing device 716 may include other components (not shown), such as memory, storage devices, network adapters, and the like. In one embodiment, the processing device 716 generates digital diagnostic images in a standard format such as the Digital Imaging and Communications in Medicine (DICOM) format. In other embodiments, the processing device 716 may generate other standard or non-standard digital image formats.

Additionally, the processing device 716 may transmit diagnostic image files such as DICOM files to the treatment planning system 730 over a data link 760. The data link 760 may be a direct link, a local area network (LAN) link, a wide area network (WAN) link such as the Internet, or another type of data link. Furthermore, the information transferred between the diagnostic imaging system 710 and the treatment planning system 730 may be either pulled or pushed across the data link 760, such as in a remote diagnosis or treatment planning configuration. For example, a user may utilize embodiments of the present invention to remotely diagnose or plan treatments despite the existence of a physical separation between the system user and the patient.

The illustrated treatment planning system 730 includes a processing device 732, a system memory device 734, an electronic data storage device 736, a display device 738, and an input device 740. The processing device 732, system memory 734, storage 736, display 738, and input device 740 may be coupled together by one or more communication channel 742 such as a bus.

The processing device 732 receives and processes image data. The processing device 732 also processes instructions and operations within the treatment planning system 730. In certain embodiments, the processing device 732 includes one or more general-purpose processors (e.g., a microprocessor), special purpose processors such as a digital signal processor (DSP), or other types of devices such as a controller or field programmable gate array (FPGA).

In particular, the processing device 732 may be configured to execute instructions for performing treatment operations discussed herein. For example, the processing device 732 may identify a non-linear path of movement of a target within a patient and develop a non-linear model of the non-linear path of movement. In another embodiment, the processing device 732 develops the non-linear model based on multiple position points and multiple direction indicators. In another embodiment, the processing device 732 generates multiple correlation models and selects one of the models to derive a position of the target. Furthermore, the processing device 732 may facilitate other diagnosis, planning, and treatment operations related to the operations described herein.

In one embodiment, the system memory 734 includes a random access memory (RAM) or other dynamic storage devices. As described above, the system memory 734 may be coupled to the processing device 732 by the communication channel 742. In one embodiment, the system memory 734 stores information and instructions to be executed by the processing device 732. The system memory 734 may also be used for storing temporary variables or other intermediate information during execution of instructions by the processing device 732. In another embodiment, the system memory 734 includes a read only memory (ROM) or other static storage devices for storing static information and instructions for the processing device 732.

In one embodiment, the storage 736 is representative of one or more mass storage devices (e.g., a magnetic disk drive, tape drive, optical disk drive, etc.) to store information and instructions. The storage 736 and the system memory 734 also may be referred to as machine readable media. In a specific embodiment, the storage 736 stores instructions to perform the modeling operations discussed herein. For example, the storage 736 may store instructions to acquire and store data points, acquire and store images, identify non-linear paths, develop linear or non-linear correlation models, and so forth. In another embodiment, the storage 736 includes one or more databases.

The display 738 may be a cathode ray tube (CRT) display, a liquid crystal display (LCD), or another type of display device. The display 738 displays information (e.g., a two-dimensional or 3D representation of the VOI) to a user. The input device 740 may include one or more user interface devices such as a keyboard, mouse, trackball, or similar device. The input device(s) 740 may also be used to communicate directional information, to select commands for the processing device 732, to control cursor movements on the display 738, and so forth.

Although one embodiment of the treatment planning system 730 is described herein, the described treatment planning system 730 is only representative of an exemplary treatment planning system 730. Other embodiments of the treatment planning system 730 may have many different configurations and architectures and may include fewer or more components. For example, other embodiments may include multiple buses, such as a peripheral bus or a dedicated cache bus. Furthermore, the treatment planning system 730 also may include Medical Image Review and Import Tool (MIRIT) to support DICOM import so that images can be fused and targets delineated on different systems and then imported into the treatment planning system 730 for planning and dose calculations. In another embodiment, the treatment planning system 730 also may include expanded image fusion capabilities that allow a user to plan treatments and view dose distributions on any one of the various imaging modalities such as MRI, CT, PET, and so forth. Furthermore, the treatment planning system 730 may include one or more features of convention treatment planning systems.

In one embodiment, the treatment planning system 730 shares a database on the storage 736 with the treatment delivery system 750 so that the treatment delivery system 750 may access the database prior to or during treatment delivery. The treatment planning system 730 may be linked to treatment delivery system 750 via a data link 770, which may be a direct link, a LAN link, or a WAN link, as discussed above with respect to data link 760. Where LAN, WAN, or other distributed connections are implemented, any of components of the treatment system 700 may be in decentralized locations so that the individual systems 710, 730 and 750 may be physically remote from one other. Alternatively, some or all of the functional features of the diagnostic imaging system 710, the treatment planning system 730, or the treatment delivery system 750 may be integrated with each other within the treatment system 700.

The illustrated treatment delivery system 750 includes a radiation source 752, an imaging system 754, a processing device 756, and a treatment couch 758. The radiation source 752, imaging system 754, processing device 756, and treatment couch 758 may be coupled to one another via one or more communication channels 760. One example of a treatment delivery system 750 is shown and described in more detail with reference to FIG. 2.

In one embodiment, the radiation source 752 is a therapeutic or surgical radiation source 752 to administer a prescribed radiation dose to a target volume in conformance with a treatment plan. In one embodiment, the radiation source 752 is the LINAC 203, as described herein. Alternatively, the radiation source 752 may be other types of radiation sources known by those of ordinary skill in the art. For example, the target volume may be an internal organ, a tumor, a region. As described above, reference herein to the target, target volume, target region, target area, or internal target refers to any whole or partial organ, tumor, region, or other delineated volume that is the subject of a treatment plan.

In one embodiment, the imaging system 754 of the treatment delivery system 750 captures intra-treatment images of a patient volume, including the target volume, for registration or correlation with the diagnostic images described above in order to position the patient with respect to the radiation source. Similar to the diagnostic imaging system 710, the imaging system 754 of the treatment delivery system 750 may include one or more sources and one or more detectors.

The treatment delivery system 750 may include a processing device 756 to control the radiation source 752, the imaging system 754, and a treatment couch 758, which is representative of any patient support device. In one embodiment, the treatment couch 758 is the treatment couch 206 coupled to a robotic arm, such as robotic arm 202. Alternatively, other types of patient support devices can be used. In one embodiment, the radiation source 752 is coupled to a first robotic arm (e.g., robotic arm 102), and the treatment couch 758 is coupled to a second robotic arm (not illustrated). The first and second robotic arms may be coupled to the same controller (e.g., controller) or to separate controllers. In one embodiment, the first and second robotic arms are identical robotic arms. In one embodiment, each of the first and second robotic arms includes four or more DOF. Alternatively, the first and second robotic arms may include dissimilar number and types of DOF. In another embodiment, the first and second robotic arms are dissimilar types of robotic arms. Alternatively, only the first robotic arm is used to move the LINAC 203 with respect to the treatment couch 206.

The processing device 756 may include one or more general-purpose processors (e.g., a microprocessor), special purpose processors such as a digital signal processor (DSP), or other devices such as a controller or field programmable gate array (FPGA). Additionally, the processing device 756 may include other components (not shown) such as memory, storage devices, network adapters, and the like.

The illustrated treatment delivery system 750 also includes a user interface 762 and a measurement device 764. In one embodiment, the user interface 762 is the user interface 700. Alternatively, other user interfaces may be used. In one embodiment, the user interface 762 allows a user to interface with the treatment delivery system 750. In particular, the user interface 762 may include input and output devices such as a keyboard, a display screen, and so forth. The measurement device 764 may be one or more devices that measure external factors such as the external factors described above, which may influence the radiation that is actually delivered to the target region. Some exemplary measurement devices include a thermometer to measure ambient temperature, a hygrometer to measure humidity, a barometer to measure air pressure, or any other type of measurement device to measure an external factor.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of radiation beam(s).

Unless stated otherwise as apparent from the discussion herein, it will be appreciated that terms such as "segmenting," "generating," "registering," "determining," "aligning," "positioning," "processing," "computing," "selecting," "estimating," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. It will be apparent from the foregoing description that aspects of the present invention may be embodied, at least in part, in software. That is, the techniques may be carried out in a computer system or other data processing system in response to its processor, such as processing device 832 or 802, for example, executing sequences of instructions contained in a memory, such as system memory 834, for example. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

In various embodiments, hardware circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller, such as the processing device 702 or 732.

A machine-readable storage medium can be used to store software and data which when executed by a data processing system causes the system to perform various methods of the present invention. This executable software and data may be stored in various places including, for example, system memory 834 and storage 836 or any other device that is capable of storing software programs and data.

Thus, a machine-readable storage medium includes any mechanism that stores information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM); random access memory (RAM); magnetic disk storage media; optical storage media; non-volatile memory devices; etc.), or the like.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A method, comprising:
    generating a first synthetically-generated image, comprising a segmented anatomical feature in a volume of interest (VOI), from three-dimensional (3D) imaging data, wherein the segmented anatomical feature substantially excludes a pathological anatomy;
    acquiring a first image of the VOI, wherein the first image comprises the segmented feature and the patholigical anatomy; and
    subtracting, by a processing device, the first synthetically-generated image from the first aquired image to substantially remove the segmented anatomical feature.

2. The method of claim 1, further comprising adjusting a first image contrast of the first synthetically-generated image to match a second image contrast of the first acquired image.

3. The method of claim 2, wherein adjusting the first image contrast to match the second image contrast comprises:
    performing a local histogram equalization algorithm; and
    performing an intensity correction on the first synthetically-generated image to match an intensity mapping of the first acquired image in the VOI.

4. The method of claim 1, further comprising:
    generating a second synthetically-generated image, including the pathological anatomy, from the 3D imaging data; and
    registering the second synthetically-generated image with the first acquired image without the segmented anatomical feature.

5. The method of claim 1, wherein the first acquired image is a two-dimensional (2D) projection of the VOI in real-time.

6. The method of claim 1, wherein generating the first synthetically-generated image comprises:
    segmenting the VOI from the 3D imaging data to obtain the segmented anatomical feature; and
    generating a digitally reconstructed radiograph (DRR) from 3D transformations of the segmented anatomical feature in each of two or more projections, wherein the DRRs in each of the two or more projections are synthetically-generated images.

7. The method of claim 6, wherein the VOI comprises a set of 2D contours in one or more views of the 3D imaging data.

8. The method of claim 6, wherein segmenting the VOI comprises generating a 3D voxel mask, wherein the voxel mask is configured to delineate the anatomical feature and to exclude other anatomical features external to the anatomical feature.

9. The method of claim 8, wherein the 3D voxel mask is generated from a set of 2D contours.

10. The method of claim 8, wherein the 3D voxel mask comprises a plurality of multi-bit voxel masks, wherein each bit in a multi-bit voxel mask corresponds to a different VOI.

11. The method of claim 4, wherein generating the first and second synthetically-generated images comprises:
    segmenting the VOI from the 3D imaging data to obtain the segmented anatomical feature and the pathological anatomy;
    generating a first digitally reconstructed radiograph (DRR) from 3D transformations of the segmented anatomical feature in each of two or more projections; and
    generating a second DRR from 3D transformations of the pathological anatomy without the segmented anatomical feature in each of two or more projections, wherein the first and second DRRs in each of the two or more projections are synthetically-generated images.

12. The method of claim 11, wherein registering the second synthetically-generated image without the segmented anatomical feature with the first acquired image comprises converting the image geometry of the second synthetically-generated image to the image geometry of the first acquired image.

13. The method of claim 11, wherein registering the second synthetically-generated image without the segmented anatomical feature with the first acquired image comprises:
    comparing the second DRR in each projection with the corresponding first acquired image to produce a first similarity measure in each projection, and wherein the first acquired image is a two-dimensional (2D) in-treatment image; and
    computing a 3D rigid transformation corresponding to a first maximum similarity measure in each projection.

14. The method of claim 11, further comprising:
    acquiring a second image of the VOI; and
    registering the first synthetically-generated image with the second acquired image.

15. The method of claim 14, wherein registering the first synthetically-generated image with the second acquired image comprises converting the image geometry of the first synthetically-generated image to the image geometry of the second acquired image.

16. The method of claim 14, wherein registering the first synthetically-generated image with the second acquired image comprises:
    comparing the first DRR in each projection with the corresponding second acquired image to produce a second similarity measure in each projection, and wherein the second acquired image is a two-dimensional (2D) in-treatment image; and
    computing a 3D rigid transformation corresponding to a second maximum similarity measure in each projection.

17. The method of claim 16, wherein the first and second maximum similarity measures each corresponds to registration between the corresponding DRR in each projection and the corresponding 2D in-treatment image, further comprising computing the 3D rigid transformation from a transformation between the corresponding DRR in each projection and the corresponding 2D in-treatment image.

18. The method of claim 16, wherein the first and second similarity measures in each projection comprises a vector displacement field between the corresponding DRR and the corresponding 2D in-treatment image.

19. The method of claim 18, further comprising determining an average rigid transformation of the segmented VOI from the vector displacement field in each projection.

20. The method of claim 19, further comprising conforming relative positions of the pathological anatomy and a radiation treatment source to a radiation treatment plan.

21. The method of claim 16, wherein computing the 3D rigid transformation corresponding to the first or second maximum similarity measure in each projection comprises:
    computing a similarity measure between a DRR in each projection and the corresponding 2D in-treatment image; and
    selecting a transformation of the 3D segmented region from the similarity measure that generates another DRR in each projection having an increased similarity measure with the corresponding 2D in-treatment image.

22. The method of claim 1, further comprising:
    determining 3D coordinates of the pathological anatomy; and
    positioning a radiation treatment beam source using the 3D coordinates of the pathological anatomy such that a radiation beam emitted from the radiation treatment beam source is directed to the pathological anatomy.

23. The method of claim 1, further comprising:
    determining 3D coordinates of the pathological anatomy; and
    positioning a patient using the 3D coordinates of the pathological anatomy such that a radiation beam emitted from a radiation treatment beam source is directed to the pathological anatomy.

24. The method of claim 1, further comprising obtaining the 3D imaging data from a medical imaging system.

25. The method of claim 1, wherein the 3D imaging data comprises one or more of computed tomography (CT) image data, magnetic resonance (MR) image data, positron emission tomography (PET) image data, and 3D rotational angiography (3DRA) image data for treatment planning.

26. The method of claim 1, wherein the segmented anatomical feature is a bony structure.

27. The method of claim 1, wherein the segmented anatomical feature is a muscular structure.

28. The method of claim 1, wherein the first acquired image is an in-treatment x-ray image.

29. A machine-accessible medium including data that, when accessed by a machine, cause a processing device of the machine to perform operations comprising:
    generating a first synthetically-generated image, including a segmented anatomical feature in a volume of interest (VOI), from three-dimensional (3D) imaging data, wherein the segmented anatomical feature substantially excludes a pathological anatomy;
    acquiring a first image of the VOI, wherein the first image comprises the segmented feature and the pathological anatomy; and
    subtracting, by a process device, the first synthetically-generated image from the first aquired image to substantially remove the segmented anatomical feature.

30. The machine accessible medium of claim 29, wherein the machine-accessible medium further includes data that cause the machine to perform operations, comprising:
    adjusting a first image contrast of the first synthetically-generated image to match a second image contrast of the first acquired image by performing a local histogram equalization algorithm;
    generating a second synthetically-generated image, including the pathological anatomy, from the 3D imaging data; and
    registering the second synthetically-generated image with the first acquired image without the segmented anatomical feature.

31. The machine accessible medium of claim 30, wherein generating the first and second synthetically-generated images comprises:
    segmenting the VOI from the 3D imaging data to obtain the segmented anatomical feature and the pathological anatomy;
    generating a first digitally reconstructed radiograph (DRR) from 3D transformations of the segmented anatomical feature in each of two or more projections; and
    generating a second DRR from 3D transformations of the pathological anatomy in each of two or more projections, wherein the first and second DRRs in each of the two or more projections are synthetically-generated images.

32. The machine accessible medium of claim 29, wherein the machine-accessible medium further includes data that cause the machine to perform operations, comprising:
    acquiring a second image of the VOI; and
    registering the first synthetically-generated image with the second acquired image.

33. The machine accessible medium of claim 29, wherein the machine-accessible medium further includes data that cause the machine to perform operations, comprising:
- determining 3D coordinates of the pathological anatomy; and
- positioning a radiation beam treatment source or a patient using the 3D coordinates of the pathological anatomy such that a radiation beam emitted from a radiation treatment beam source is directed to the pathological anatomy.

34. The machine accessible medium of claim 29, wherein the machine-accessible medium further includes data that cause the machine to perform operations, comprising obtaining the 3D imaging data from a medical imaging system, wherein the 3D imaging data comprises one or more of computed tomography (CT) image data, magnetic resonance (MR) image data, positron emission tomography (PET) image data, and 3D rotational angiography (3DRA) image data for treatment planning.

35. An apparatus, comprising
- a first processing device to receive a first synthetically-generated image, comprising a segmented anatomical feature in a volume of interest (VOI), generated from three dimensional (3D) imaging data, and a first acquired image of the VOI, wherein the segmented anatomical feature substantially excludes a pathologic anatomy and wherein the first image comprises the segmented feature and the pathological anatomy, and wherein the first processing device is configured to subtract the first synthetically-generated image from the first acquired image to substantially remove the segmented anatomical feature.

36. The apparatus of claim 35, wherein the first processing device is configured to adjust first image contrast of the first synthetically-generated image to match a second image contrast of the first acquired image by performing a local histogram equalization algorithm.

37. The apparatus of claim 36, wherein the first processing device is part of a treatment delivery system, and wherein the apparatus further comprises a treatment planning system coupled to the treatment delivery system, wherein the treatment planning system comprises a second processing device to segment the VOI, having the pathological anatomy, from three-dimensional (3D) scan data to obtain a segmented VOI, wherein the 3D imaging data includes a pathological anatomy, and wherein the second processing device is further configured to generate the first synthetically-generated image, including the segmented anatomical feature in the VOI.

38. The apparatus of claim 37, wherein the second processing device is configured to generate a second synthetically-generated image, including the pathological anatomy, from the 3D imaging data, and wherein the first processing device is configured to receive the second synthetically-generated image from the second processing device and to register the second synthetically-generated image with the first acquired image without the segmented anatomical feature.

39. The apparatus of claim 38, wherein the treatment delivery system further comprises an imaging system having a pair of imagers and corresponding detectors to acquire the first acquired image.

40. The apparatus of claim 38, wherein the first processing device is further configured to determine an average rigid transformation of the 3D image data and a 3D displacement of the pathological anatomy and to apply image-guided radiation treatment to the pathological anatomy.

41. The apparatus of claim 38, further comprising a diagnostic imaging system coupled to the treatment planning system, the diagnostic imaging system having a third processing device to obtain the 3D imaging data.

42. The apparatus of claim 41, wherein the first processing device, the second processing device and the third processing device are the same processing device.

43. An apparatus, comprising:
- means for generating a first synthetically-generated image comprising a segmented anatomical feature in a volume of interest (VOI) from three-dimensional (3D) imaging data, wherein the segmented anatomical feature substantially excludes a pathological anatomy; and
- means for subtracting the first synthetically-generated image from an acquired image using a processing device to substantially remove the segmented anatomical feature, wherein the first image comprises the segmented feature and the pathological anatomy.

44. The apparatus of claim 43, further comprising means for adjusting a first image contrast of the first synthetically-generated image to match a second image contrast of the acquired image.

* * * * *